(12) United States Patent
Marshall et al.

(10) Patent No.: US 7,933,662 B2
(45) Date of Patent: Apr. 26, 2011

(54) MEDICAL ELECTRICAL LEAD INCLUDING AN INDUCTANCE AUGMENTER

(76) Inventors: Mark T. Marshall, Forest Lake, MN (US); Henry D. Schroder, St. Louis Park, MN (US)

(*) Notice: Subject to any disclaimer, the term of this patent is extended or adjusted under 35 U.S.C. 154(b) by 1362 days.

(21) Appl. No.: 11/380,259

(22) Filed: Apr. 26, 2006

(65) Prior Publication Data

US 2007/0255377 A1     Nov. 1, 2007

(51) Int. Cl.
*A61N 1/04* (2006.01)
(52) U.S. Cl. .................... 607/127; 607/116; 607/122
(58) Field of Classification Search .......... 607/116, 607/122, 127
See application file for complete search history.

(56) References Cited

U.S. PATENT DOCUMENTS

| 4,038,990 | A | * | 8/1977 | Thompson | 607/9 |
|---|---|---|---|---|---|
| 5,076,285 | A | | 12/1991 | Hess et al. | |
| 5,217,010 | A | * | 6/1993 | Tsitlik et al. | 607/9 |
| 6,535,093 | B1 | * | 3/2003 | Murata et al. | 336/83 |
| 2002/0116029 | A1 | | 8/2002 | Miller et al. | |
| 2003/0083726 | A1 | | 5/2003 | Zeijlemaker et al. | |
| 2003/0144720 | A1 | | 7/2003 | Villaseca et al. | |
| 2005/0222656 | A1 | | 10/2005 | Wahlstrand et al. | |
| 2005/0222659 | A1 | | 10/2005 | Olsen et al. | |
| 2005/0246007 | A1 | * | 11/2005 | Sommer et al. | 607/127 |
| 2006/0229693 | A1 | * | 10/2006 | Bauer et al. | 607/116 |

* cited by examiner

*Primary Examiner* — Carl H Layno
*Assistant Examiner* — Natasha N Patel
(74) *Attorney, Agent, or Firm* — Stephen W. Bauer; Reed A. Duthler

(57) ABSTRACT

A medical electrical lead includes an inductance augmenter assembly. The assembly includes an inductor coil formed of an insulated wire, which is wound about a non-conductive core and is electrically coupled in series between a conductor coil of the lead and an electrode of the lead.

27 Claims, 6 Drawing Sheets

MEDICAL ELECTRICAL LEAD INCLUDING AN INDUCTANCE AUGMENTER

TECHNICAL FIELD

The present invention pertains to medical electrical leads and more particularly to medical electrical leads including inductor elements.

BACKGROUND

Implanted medical devices often include elongate medical electrical leads carrying at least one conductor electrically coupled to a tissue-contacting electrode; examples of such devices include, but are not limited to, pacemakers, cardioverter-defibrillators and neurostimulators. It is known in the art that medical electrical leads can act as antennas, which 'pick up' electromagnetic radiation of radio-frequency (RF) pulses, for example used for Magnetic Resonance Imaging (MRI), and that these pulses can induce a appreciable amount of current in lead conductors. When this current is induced in a lead conductor, a relatively large current gradient can develop across the resistive interface between the electrode of that conductor and the tissue interfacing with the electrode; such a gradient causes heat to be released into the tissue, which may be injurious to the tissue.

It is further known in the art to insert, in series, an electromagnetic trap, in the form of an inductor element, between the conductor of a lead and the tissue-contacting electrode. The inductor element acts as a high-frequency resistor attenuating RF pulse-induced current flowing to the electrode and thereby reduces undesirable tissue heating. Although such inductor elements have been proposed for medical electrical leads, there is still a need for practical designs which integrate such an element into medical leads without compromising other lead features, for example, pertaining to ease of implantation, stable fixation and long term performance of the lead.

Many medical electrical leads include elongate conductor coils coupled to tissue-contacting electrodes. In some cases, these conductor coils may be designed to have inductive properties that effectively reduce the undesirable tissue heating described above. However, in other cases, for example, when the conductor coil must be stiff enough to transfer torque in order to steer a lead to, and/or fix a lead electrode at, a target site, it may not be possible for the coil to have the inductive properties that reduce tissue heating.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
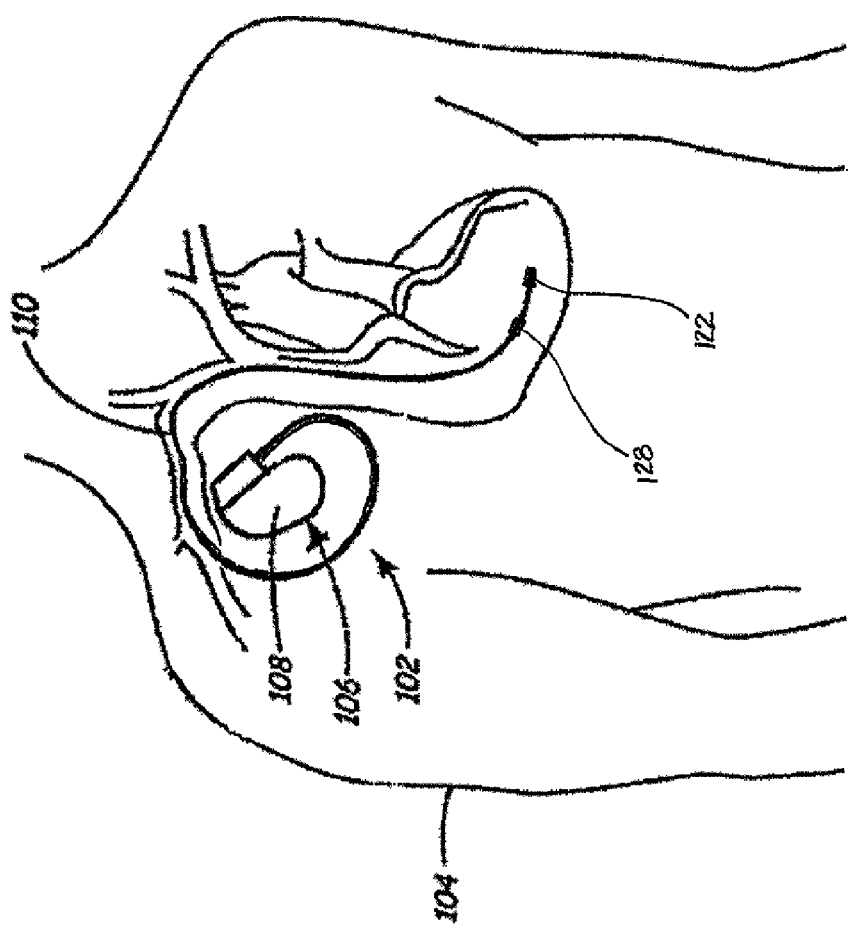
FIG. 1 is a schematic of an exemplary medical system including a medical electrical lead.
Figure 2A:
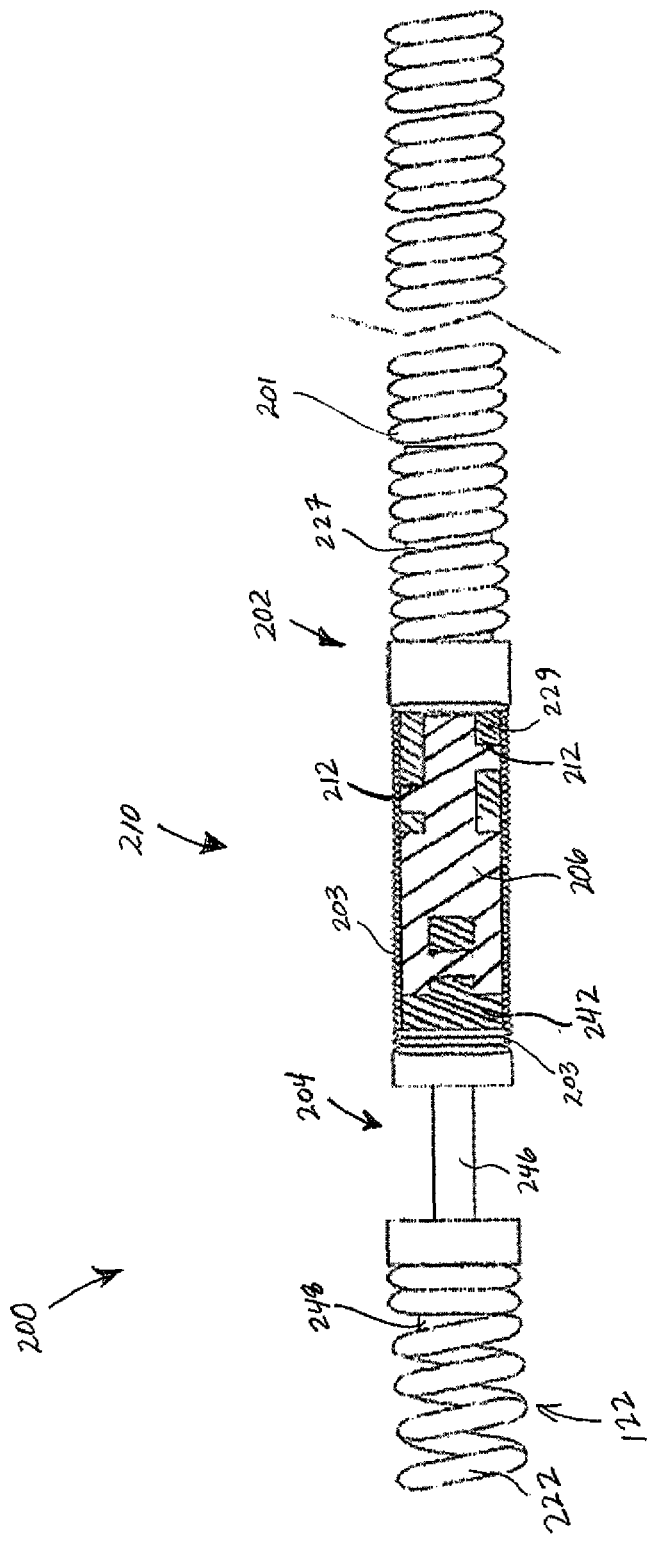
FIG. 2A is a plan view, with a partial section, of an electrode assembly, according to one embodiment of the present invention.

FIG. 1 is a schematic of an exemplary medical system 102 implanted in a patient 104. FIG. 1 illustrates medical system 102 including an electronic medical device 106 contained in an hermetically sealed housing 108 and coupled to a medical electrical lead 110. FIG. 1 further illustrates lead 110 including a tip electrode 122 and a more proximally located electrode 128, both positioned in a right ventricle of patient 104; tip electrode 122 contacts tissue in the right ventricle, primarily for delivery of pacing stimulation from device 106. Electrode 128 may form a bipolar pair with tip electrode 122, for pacing and sensing, may be an independent defibrillation electrode, or may function both for defibrillation and bipolar pacing and sensing. As previously described, lead 110 may act as an antenna picking up electromagnetic radiation of radio-frequency (RF) pulses used for MRI. According to embodiments of the present invention, an electrical circuit of lead 110, which couples electrode tip 122 to device 106, includes an inductance augmenter, such that an inductance of the circuit is at least greater than approximately one micro Henry (μH), and, preferably, approaching approximately 4 μH. Inductances greater than approximately one μH have been shown to reduce the resultant current gradient across the electrode-tissue interface and thereby reduce undesirable tissue heating, but increasing the inductance needs to be balanced with circuit resistance, which typically should not exceed approximately 150 ohms for efficient pacing performance. FIG. 2A illustrates one embodiment of such an electrical circuit or electrode assembly.

Figure 2B:
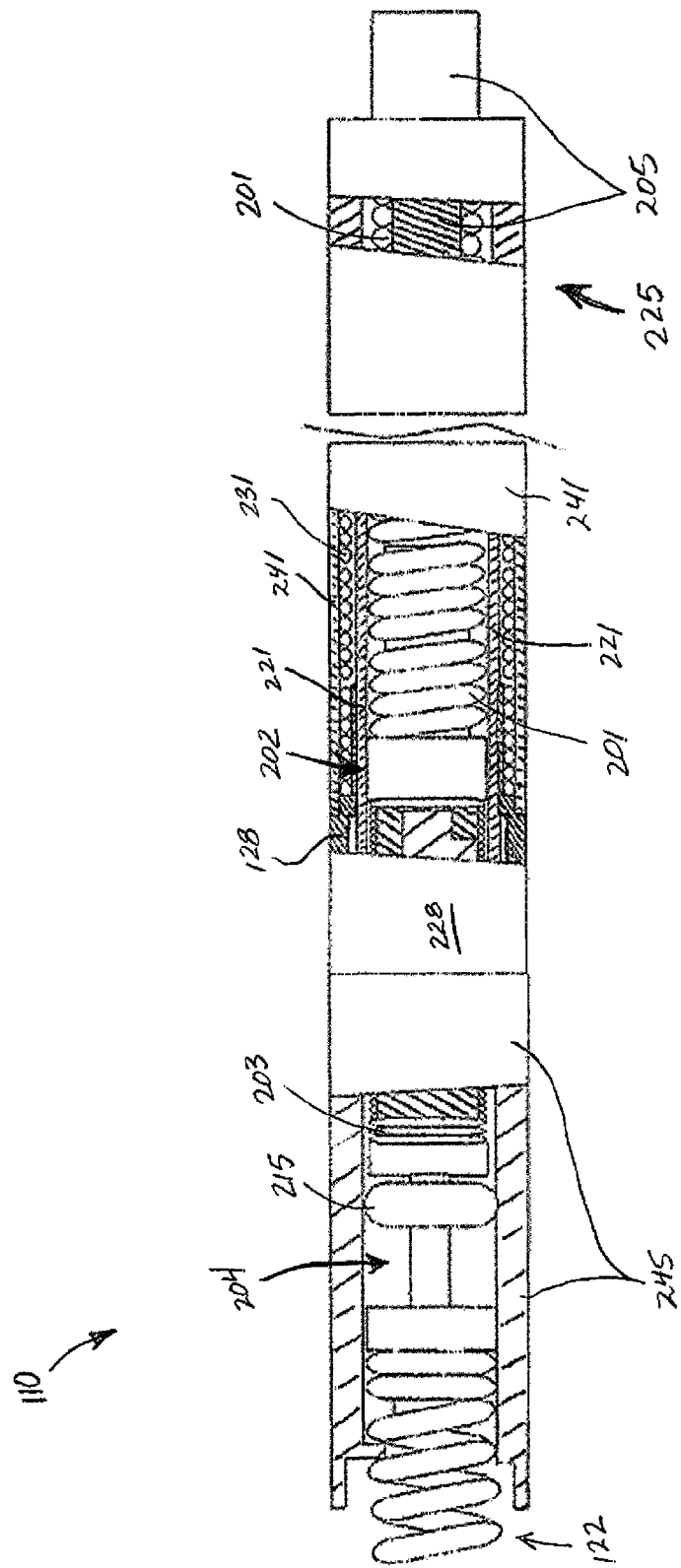
FIG. 2B is a plan view, with partial sections, of a lead including the assembly of FIG. 2A, according to some embodiments of the present invention.

FIG. 2A is a plan view, with a partial section, of an electrode assembly 200, according to one embodiment of the present invention; and FIG. 2B is a plan view, with partial sections, of lead 110 including assembly 200, according to some embodiments of the present invention. FIG. 2A illustrates assembly 200 including an inductance augmenter 210 electrically coupled in series between an elongate conductor coil 201 and electrode 122; electrode 122 is shown including an electrode surface 222 in proximity to a distal tip thereof for tissue contact; a sharpened distal tip (not shown) and the helical form of electrode 122, well known to those skilled in the art, facilitates fixation of electrode at an implant site via a screw-in method. According to preferred embodiments of the present invention, conductor coil 201 is designed to efficiently transfer torque from a proximal end to a distal end thereof in order to screw in electrode 122; such a conductor coil may have a diameter between approximately 0.025 inch and approximately 0.035 inch and, although is shown herein formed of four wire filars, may have as few as 2 filars and as many as six filars, each of which having a diameter between approximately 0.004 inch and approximately 0.007 inch. Because inductances of such coils are less than one μH, for lengths ranging from approximately 30 cm to approximately 70 cm, which are typical for medical electrical leads, an inductance augmenter, for example, inductance augmenter 210, is necessary. It should be noted that conductor coils described herein may be formed from silver-cored or non-silver-cored MP35N wire, or tantalum, known to those skilled in the art, and electrodes/electrode surfaces from platinum or platinum-iridium alloy, also known to those skilled in the art.

FIG. 2B illustrates lead 110 including electrode assembly 200 as an extendable-retractable assembly, wherein the proximal end of conductor coil 201 is coupled, within a connector 225, to a connector pin 205; in addition to providing an electrical contact surface for coupling with device 106 (FIG. 1), pin 205 may be grasped in order to rotate coil 201 and thereby screw electrode 122 into an implant site. Methods and arrangements of lead components suitable for connector 225 may be any of those known to those skilled in the art for extendable-retractable type leads. FIG. 2B further illustrates a coaxial arrangement of conductor coil 201 extending within an outer conductor coil 231, being electrically isolated from outer conductor coil 231 by a layer of inner insulation 221. Outer conductor coil 231 is shown extending within a layer of outer insulation 241 to a distal end, which is mounted on, and coupled to, an internal projection of electrode 128, for example, via crimping or laser welding; an electrode surface 228 of electrode 128 is exposed external to the projection and has approximately the same outer diameter as outer insulation 241. According to an exemplary embodiment, the outer diameter of outer insulation 241 and electrode surface 228 is about 6 French or between approximately 0.07 inch and approximately 0.085 inch. FIG. 2B further illustrates inner insulation 221 extending over a proximal portion of inductance augmenter 210 and a distal insulator member 245 extending over a distal portion of inductance augmenter 210 and having an outer diameter approximately equal to the outer diameter of electrode surface 228; inner insulation 221 and insulator member 245 join together beneath electrode surface 228 to complete the electrical isolation of augmenter 210 from electrode 128. Those skilled in the art will appreciate that distal insulator member 245 forms a sleeve head from which, and into which, electrode 122 may be extended and retracted, respectively, and includes a seal, for example sealing member 215, to preventingress of bodily fluids. Those skilled in the art will further appreciate that, in order to extend and retract electrode 122, inductance augmenter 210 should be torsionally coupled to coil 201 and to electrode 122. The term 'torsionally coupled' is used herein to denote a mechanical coupling having the necessary rigidity to transfer torque, in a relatively efficient manner, and the durability to handle the torsional loading. Although preferred embodiments of the present invention include torque transfer functionality, it should be noted that the scope of the invention is not so limited, and alternate embodiments of electrode assemblies include inductance augmenters that need not transfer torque.

Referring back to FIG. 2A, inductance augmenter 210 includes an inductor coil 203 wound about a non-conductive core 206, which is coupled, at a proximal end, to a proximal conductive junction component 202, and, at a distal end, to a distal conductive junction component 204. Proximal component 202 is, in turn, coupled to conductor coil 201 and electrically couples coil 201 to inductor coil 203; and distal component 204 is coupled to electrode 122 and electrically couples coil 203 to electrode 122. FIG. 2A further illustrates distal conductive junction component 204 including a proximal protrusion 242 interlocking with core 206, a proximal stud 244 on which inductor coil is mounted for coupling, for example, via crimping or laser welding, a distal stud 248 on which electrode 122 is mounted for coupling, for example, via crimping or laser welding, and a shaft 246 extending between proximal stud 244 and distal stud 248. Proximal conductive junction component 202 is shown including a proximal stud 227 on which conductor coil 201 is mounted for coupling, for example via crimping or laser welding, and a distal stud 229 interlocking with core 206 and on which inductor coil 203 is mounted for coupling, for example, via crimping or laser welding. According to preferred embodiments, core 206 is relatively rigid to transfer torque and is torsionally coupled to components 202 and 204; core 206 is shown interlocking with proximal component 202, extending within a bore of stud 229 and through sidewall slots or holes 212, and with distal component 204, extending through hole 214. Suitable materials for core 206 include, but are not limited to, relatively hard polyurethanes, such as 55D or 75D, ceramics and Polyetheretherketones (PEEK®); and core 206 may be molded into interlocking engagement with components 202 and 204.

Figure 3A:
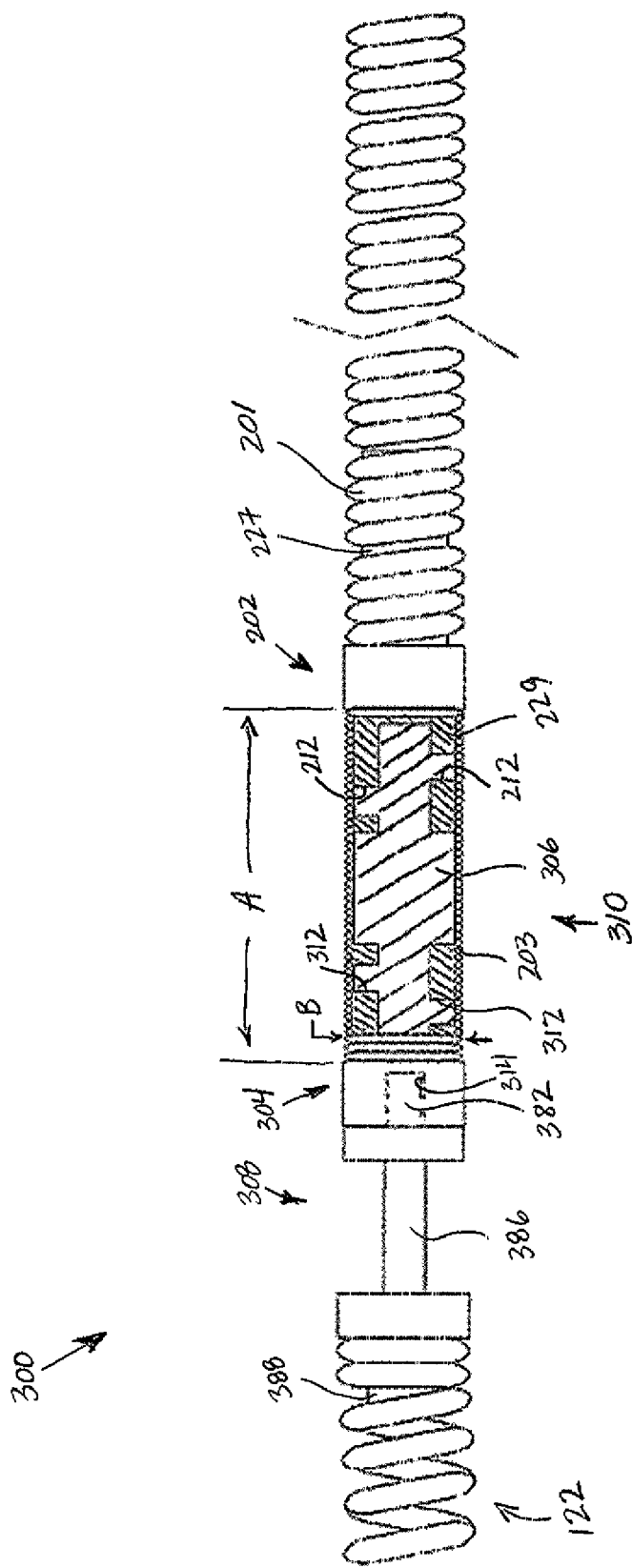
FIG. 3A is a plan view, with a partial section, of an electrode assembly, according to another embodiment of the present invention.

FIG. 3A is a plan view, with a partial section, of an electrode assembly 300, according to another embodiment of the present invention. FIG. 3A illustrates an electrode assembly 300 including an inductance augmenter 310 electrically coupled in series between conductor coil 201 and electrode 122; inductance augmenter 310 includes inductor coil 203 wound about a non-conductive core 306 and is similar to augmenter 210, previously described. According to the illustrated embodiment, two distal conductive components 304 and 308 electrically couple electrode 122 to inductor coil 203 and torsionally couple electrode 122 to core 306; core 306 extends within a bore and sidewall slots or holes 312 to interlock with component 304 in manner similar to the junction of core 306, and core 206, with component 202.

FIG. 3A further illustrates, with dashed lines, component 308 including a protrusion 382 inserted within a bore 314 of component 304 for coupling, a distal stud 388 on which electrode 122 is mounted for coupling, and a shaft 386 extending between protrusion 382 and stud 388; suitable coupling means include, but are not limited to, crimping and laser welding. Electrode assembly 300 may be incorporated into lead 110 in a manner similar to that shown for assembly 200 in FIG. 2B or may be incorporated into a lead of a different type, for example as shown in FIG. 3B.

Figure 3B:
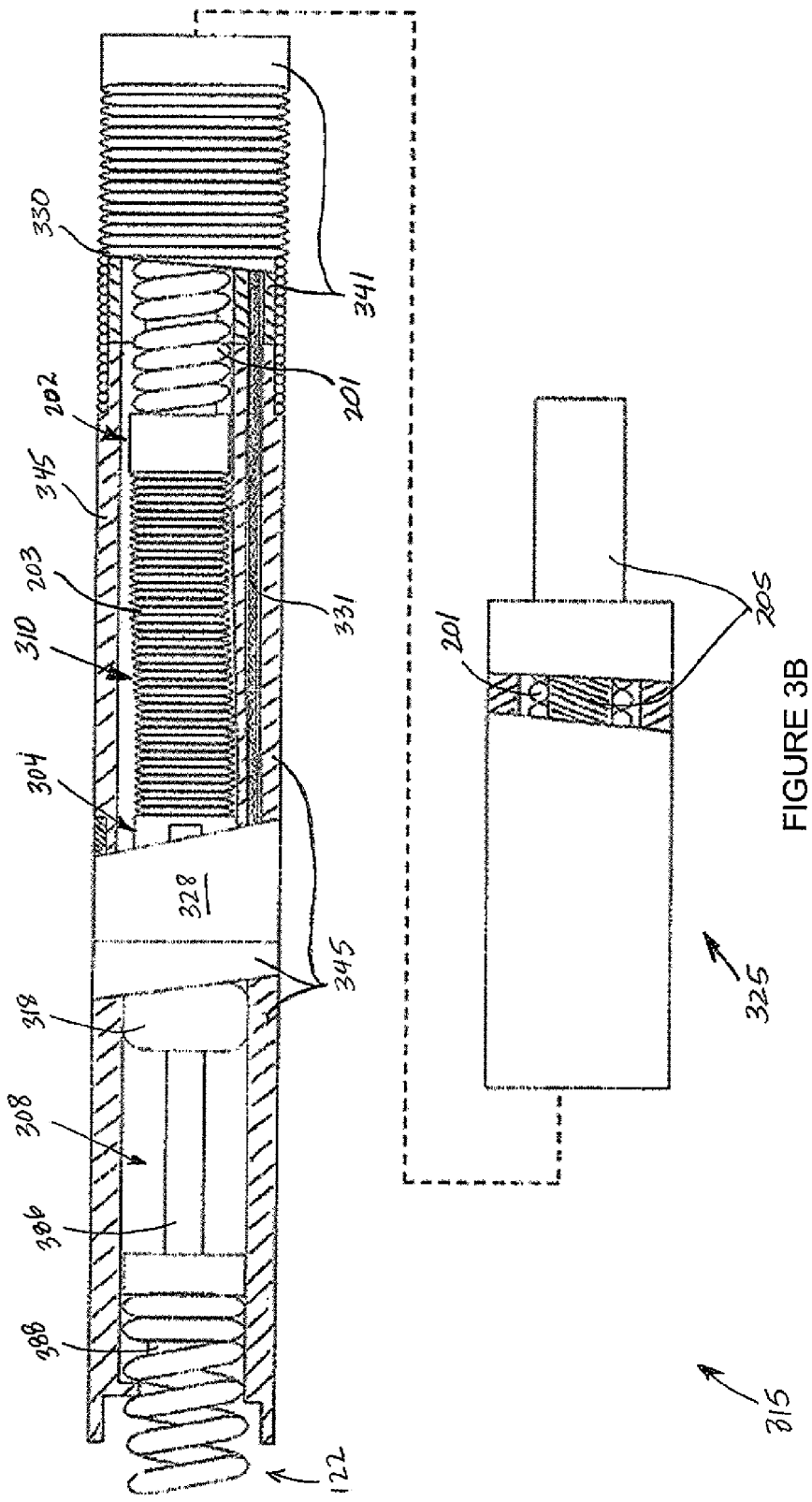
FIG. 3B is a plan view, with partial sections, of a lead including the assembly of FIG. 3A, according to some embodiments of the present invention.

FIG. 3B is a plan view, with partial sections, of a lead 315 including electrode assembly 300, according to some embodiments of the present invention. FIG. 3 illustrates assembly 300 as an extendable-retractable assembly wherein the proximal end of conductor is coupled, within a connector 325, to connector pin 205, as previously described for assembly 200 in lead 110. FIG. 3B further illustrates lead 315 including an elongate insulation tubing 341 extending distally from connector 325 and including a plurality of lumens, two of which are shown: one holding coil conductor 201, which is electrically coupled to augmenter 310, as previously described in conjunction with FIG. 2A, and another holding a cable conductor 331, which is coupled to an electrode surface 328, for example, via crimping or laser welding.

According to the illustrated embodiment, tubing 341 electrically isolates conductors 201 and 331 from one another, and from the environment external to lead 315, and is joined, for example, by adhesive bonding or welding, to a distal insulator element 345 that includes a first lumen, holding an extension of conductor 201 and inductance augmenter 310, and a second lumen, holding an extension of conductor 331. Insulator element 345 is shown extending beneath an electrode surface 328 from the junction with tubing 341 to a distal end from which electrode 122 protrudes; an outer diameter of element 345, on either side of electrode surface 328, is approximately equal to an outer diameter of surface 328, and a distal portion of element 345 houses a distal portion of assembly 300 and a sealing member 318. According to an exemplary embodiment, the outer diameter of element 345 and electrode surface 328 is about 7 French or between approximately 0.085 inch and approximately 0.1 inch. FIG. 3B further illustrates lead 315 including a coil electrode 330 extending over the junction between distal insulator element 345 and tubing 341 and proximally therefrom; those skilled in the art will appreciate that coil electrode 330 may serve as a defibrillation electrode and is electrically coupled to another conductor extending within another lumen of tubing 341 that cannot be seen in this view. Lead 315 may further include another electrode, disposed proximal to electrode 330, which may serve as a defibrillation electrode too, thus, tubing 341 may include yet another lumen for a conductor which couples to this other electrode.

Figure 4:
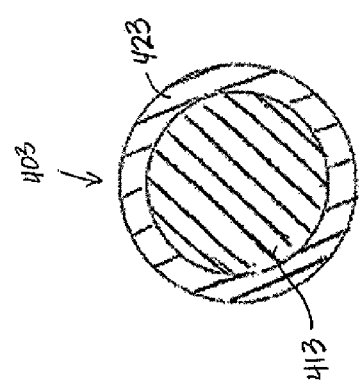
FIG. 4 is a section view through an inductor wire according to some embodiments of the present invention.

FIG. 4 is a section view through an exemplary insulated inductor wire 403 from which inductor coil 203 may be formed. FIG. 4 illustrates insulated inductor wire 403 including a conductive wire 413 over-laid with an insulating layer or coating 423; according to preferred embodiments of the present invention, wire 413 is formed of a silver-cored MP35N alloy, having up to 40% silver and a diameter ranging from approximately 0.001 inch to approximately 0.003 inch, and layer 423 is formed of Si polyimide having a thickness of approximately 0.0001 inch. The silver-cored MP35N is preferred for its relatively low resistance combined with an adequate current carrying capacity, but other suitable materials from which wire 413 may be formed include, but are not limited to, tantalum, non-silver-cored MP35N, and copper. Alternate materials for layer 423 include, but are not limited to, fluoropolymers, such as ETFE and PTFE. Insulating layer 423 around wire 403 at either end of coil 203 may be mechanically abraded away or thermally ablated away for electrical coupling with the distal and proximal conductive junction components; if laser welding is used to electrically couple coil 203, the laser energy may simultaneously weld and ablate away layer 203 at the weld.

With reference back to FIG. 3A, exemplary dimensions of coil 203, formed from preferred embodiments of wire 403, that provide a sufficient augmenting inductance to electrode assemblies, for example assemblies 200 and 300, will now be described. FIG. 3A illustrates coil 203 being close wound and having a length A and an outer diameter B. The inductance L of a coil is proportional to the number of turns, the length, and the diameter of the coil according to the following relationship: $L=(\mu N^2 A)/l$, where $\mu$ is magnetic permeability of the core about which the coil is wound, N is the number of turns of the coil, A is the cross-sectional area of the coil, and I is the length of the coil. Thus in order to achieve an inductance between approximately 0.3 μH and 0.8 μH (that which will effectively augment the inductance of conductor coils having dimensions in the ranges previously described), length A may range from approximately 0.1 inch to approximately 0.25 inch, and outer diameter B may range from approximately 0.02 inch to approximately 0.04 inch. With reference back to FIGS. 2A and 3A it may be appreciated that outer diameter D of coil 203 is approximately equal to an outer diameter of coil 201. Although such a configuration (or one in which D is less than the outer diameter of coil 201) is preferred, so as not to increase an outer diameter of the lead into which either assembly 200 or 300 are incorporated, the scope of the present invention is not so limited, and alternate embodiments may include larger diameter inductor coils. Also, it should be noted that although the figures herein illustrate coil 203 including only a single layer, alternate embodiments of the present invention include inductor coils wound in multiple layers, as is known to those skilled in the art, which may boost an inductance of the augmenter toward 4 μH.

Figure 5A:
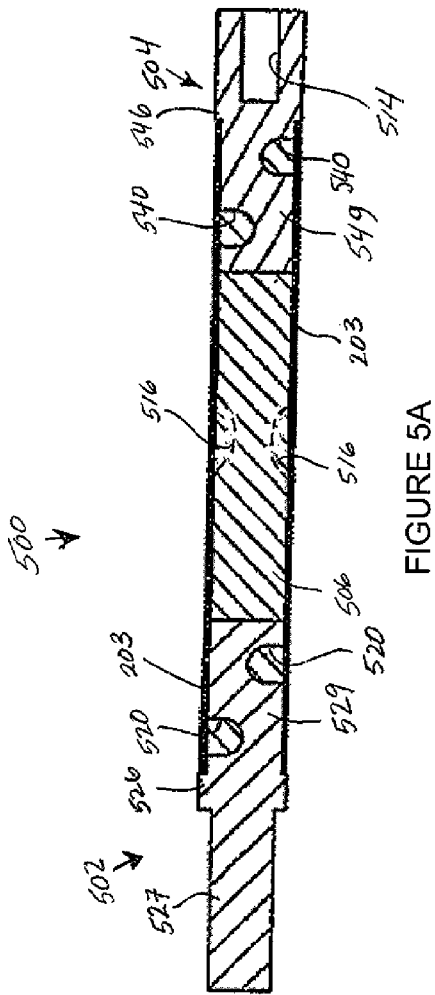
FIG. 5A is a plan view, with a partial section, of an inductance augmenter assembly, according to some embodiments of the present invention.
Figure 5B:
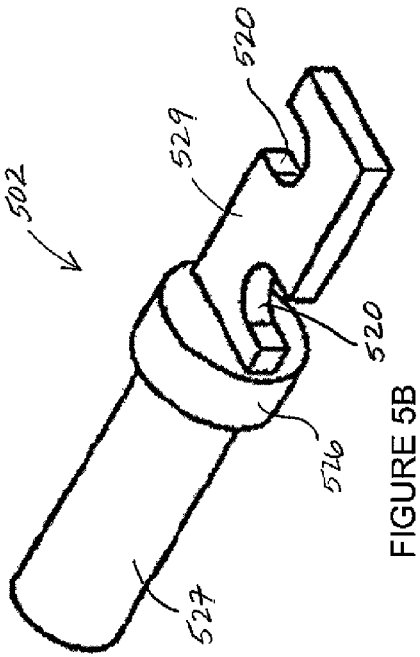
FIG. 5B is a perspective view of a component of the augmenter assembly shown in FIG. 5A.

FIG. 5A is a plan view, with a partial section, of an inductance augmenter assembly 500, according to some embodiments of the present invention; and FIG. 5B is a perspective view of a component of the augmenter assembly shown in FIG. 5A. FIG. 5A illustrates assembly 500 including inductor coil 203 electrically coupled in series between a first conductive end 502 and a second conductive end 504 and wound about a non-conductive core 506 that extends between ends 502 and 504. FIG. 5A further illustrates first end 502, which generally corresponds to proximal conductive junction component 202 shown in FIGS. 2A-3B, including a proximal stud 527 on which conductor coil 201 may be mounted for electrical coupling, and second end 504, which generally corresponds to distal conductive junction component 304 shown in FIGS. 3A-B, including a bore 514 in which protrusion 382 of distal component 308 may be inserted for electrical coupling with electrode 122. According to the illustrated embodiment, first and second ends 502 and 504 each include a relatively flat and longitudinally extending protrusion 529 and 549, respectively, which extend within core 506 to provide torsional coupling with core 506; each protrusion 529 and 549 further includes slots 520 and 540, respectively, for interlocking with core 506 to enhance a tensile strength of assembly 500. With reference to FIG. 5B, it may be appreciated that core 506 extends about each protrusion 529, 549, thereby forming a cylindrical profile about which coil 203 extends to butt up against shoulders 526 and 546 of ends 502 and 504, respectively, for electrical coupling, for example, via laser welding.

FIG. 5A further illustrates core 506 including an optional indentation 516, indicated with dashed lines; indentation 516, extending about a circumference of core 506, increases the bending flexibility core 506, without compromising torque transfer, which may be useful for implementation in some leads, for example, according to embodiments illustrated by FIG. 3B. FIG. 3B illustrates lead 315 wherein a lumen of insulator element 345 carrying a distal portion of electrode assembly 300 travels laterally from an offset opening that mates with a lumen of tubing 341, from which assembly 300 extends, to a more central location to position electrode 122 approximately along a longitudinal centerline of lead 315. According to the illustrated embodiment, inductance augmenter 310 bends along the lumen of element 345; a resilient bending flexibility of inductance augmenter 310, for example, via indentation 516 in core 306, may help to increase the efficiency of torque transfer to electrode 122. Various hinge designs, known to those skilled in the art, which facilitate resilient bending, without sacrificing torque transfer, may alternately be incorporated into inductance augmenter assemblies.

In the foregoing detailed description, the invention has been described with reference to specific embodiments. However, it may be appreciated that various modifications and changes can be made without departing from the scope of the invention as set forth in the appended claims. For example, although the present invention has been described in the context of screw-in, or active fixation, leads that require torsional coupling of inductance augmenters, the invention is not so limited; alternate embodiments of the present invention include passive fixation leads, which are known to those skilled in the art, having inductance augmenters which may or may not be torsionally coupled.

The invention claimed is:

1. A medical electrical lead, comprising:
   an insulated elongate conductor coil extending from a proximal end to a distal end;
   an electrode surface electrically coupled to the conductor coil and disposed distal to the distal end of the conductor coil;
   an inductance augmenter comprising an inductor coil formed of an insulated wire electrically coupled in series between the electrode surface and the conductor coil, the augmenter further comprising a non-conductive core about which the inductor coil is wound; and
   a distal conductive junction component coupled to the core and electrically coupling the electrode surface to the inductor coil; and
      further comprising a helical component including the electrode surface, and wherein the conductor coil, the inductance augmenter, and the distal junction component all transfer torque to the helical component, the torque being applied to the conductor coil, in proximity to the conductor coil proximal end.

2. The lead of claim 1, further comprising a proximal conductive junction component coupled to the core and electrically coupling the conductor coil to the inductor coil.

3. The lead of claim 1, wherein the distal conductive junction component includes a shaft extending between the electrode surface and the coupling with the core.

4. The lead of claim 1, further comprising:
   an electrode component including the electrode surface; and
   a shaft extending from a proximal end to a distal end, the shaft electrically coupled to the distal junction component in proximity to the shaft proximal end and to the electrode component in proximity to the shaft distal end.

5. The lead of claim 1, wherein an outer diameter of the conductor coil is approximately equal to an outer diameter of the inductor coil.

6. The lead of claim 1, wherein an inductance of the inductor coil is between approximately 0.3 µH and approximately 0.8 µH, and a combined inductance of the conductor coil and the inductor coil is greater than approximately one µH.

7. The lead of claim 1, wherein the core has some bending flexibility.

8. The lead of claim 1, further comprising:
   a second insulated elongate conductor extending alongside the conductor coil;
   a second electrode surface electrically coupled to the second conductor and disposed proximal to the electrode surface; and
   an insulator member extending over the inductance augmenter between the electrode surface and the second electrode surface.

9. The lead of claim 8, wherein an outer diameter of the second electrode surface is approximately equal to an outer diameter of the insulator member.

10. The lead of claim 8, wherein the second elongate conductor is approximately coaxial with the conductor coil.

11. An electrode assembly for a medical electrical lead, comprising:
    an elongate conductive torque coil extending from a proximal end to a distal end;
    a helix electrode electrically coupled to the torque coil and disposed distal to the distal end of the torque coil;
    an inductance augmenter comprising an inductor coil formed of an insulated wire electrically coupled in series between the electrode and the conductor coil, the augmenter further comprising a non-conductive core about which the inductor coil is wound, the core having torque-transfer capacity and being torsionally coupled to the torque coil and the electrode.

12. The assembly of claim 11, further comprising a proximal conductive junction component torsionally coupling the core to the torque coil and electrically coupling the torque coil to the inductor coil.

13. The assembly of claim 11, wherein an outer diameter of the torque coil is approximately equal to an outer diameter of the inductor coil.

14. The assembly of claim 11, wherein a combined inductance of the torque coil and the inductor coil is greater than approximately one µH.

15. The assembly of claim 11, wherein the core has some bending flexibility.

16. The assembly of claim 11, further comprising:
    a second insulated elongate conductor extending alongside the conductor coil;
    a second electrode surface electrically coupled to the second conductor and disposed proximal to the electrode surface; and
    an insulator member extending over the inductance augmenter between the electrode surface and the second electrode surface.

17. The assembly of claim 16, wherein an outer diameter of the second electrode surface is approximately equal to an outer diameter of the insulator member.

18. The assembly of claim 16, wherein the second elongate conductor is approximately coaxial with the conductor coil.

19. A medical electrical lead, comprising:
    an elongate conductive torque coil extending from a proximal end to a distal end;
    a lead body surrounding the torque coil, the torque coil rotatable within the lead body;
    a rotatable helix electrode electrically coupled to the torque coil and disposed distal to the distal end of the torque coil;
    an inductance augmenter comprising an inductor coil formed of an insulated wire electrically coupled in series between the electrode and the conductor coil, the augmenter further comprising a non-conductive core about which the inductor coil is wound, the core having torque-transfer capacity and being torsionally coupled to the torque coil and the electrode.

20. The lead of claim 19, further comprising a proximal conductive junction component torsionally coupling the core to the torque coil and electrically coupling the torque coil to the inductor coil.

21. The lead of claim 19, wherein an outer diameter of the torque coil is approximately equal to an outer diameter of the inductor coil.

22. The lead of claim 19, wherein a combined inductance of the torque coil and the inductor coil is greater than approximately one µH.

23. The lead of claim 19, wherein the core has some bending flexibility.

24. The lead of claim 19, further comprising:
    a second insulated elongate conductor extending alongside the conductor coil;

a second electrode surface electrically coupled to the second conductor and disposed proximal to the electrode surface; and an insulator member extending over the inductance augmenter between the electrode surface and the second electrode surface.

25. The lead of claim 24, wherein an outer diameter of the second electrode surface is approximately equal to an outer diameter of the insulator member.

26. The lead of claim 25, wherein the second elongate conductor is approximately coaxial with the conductor coil.

27. The lead of claim 19 wherein the torque coil comprises an insulated elongate conductor coil.

* * * * *